Feb. 12, 1957 E. B. ARNESEN Plant Pat. 1,562
CAMELLIA PLANT
Filed May 21, 1956 2 Sheets-Sheet 1
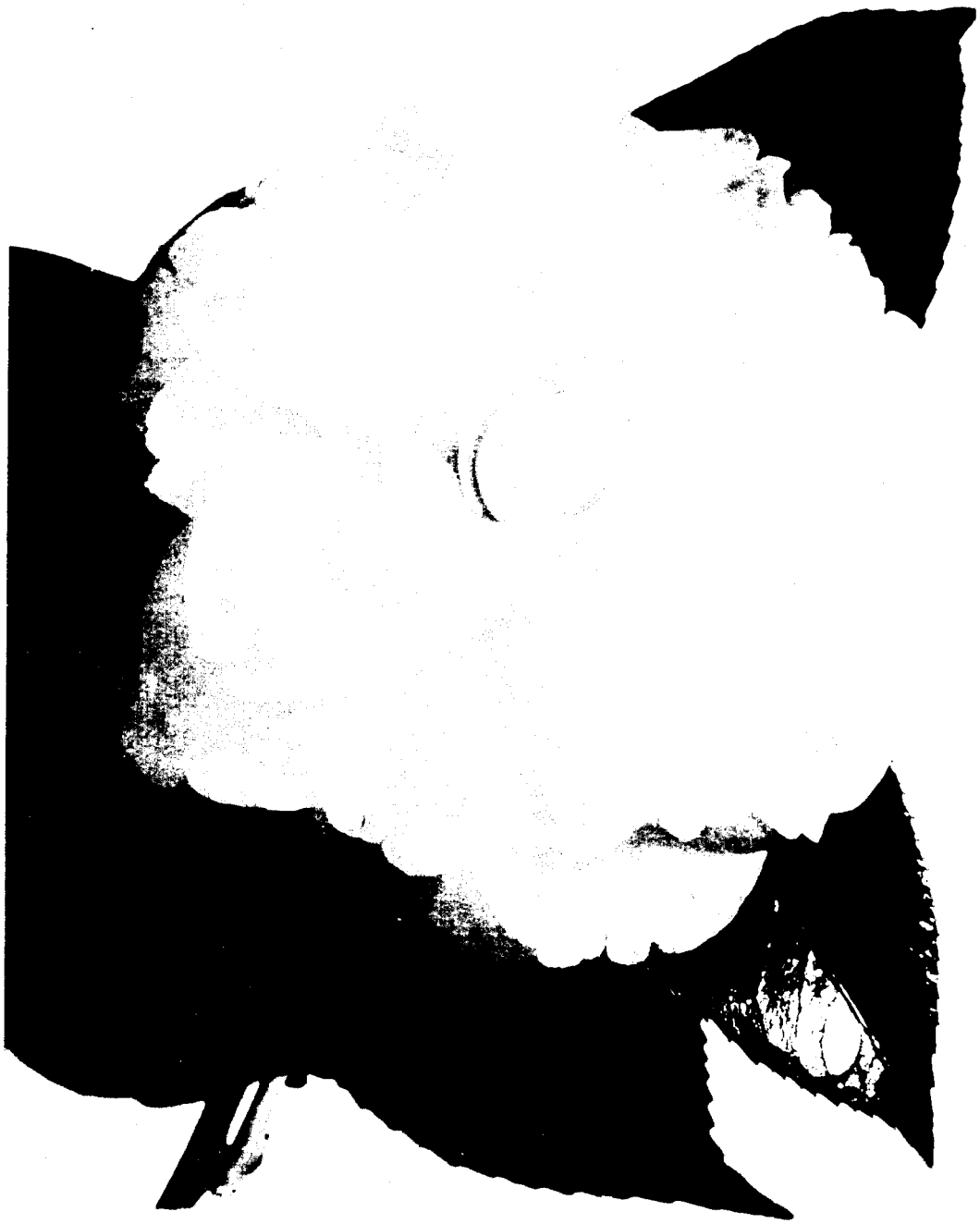
Inventor.
E. B. Arnesen
By: Robert Cobb
Attorneys.

Feb. 12, 1957 E. B. ARNESEN Plant Pat. 1,562
CAMELLIA PLANT
Filed May 21, 1956 2 Sheets-Sheet 2
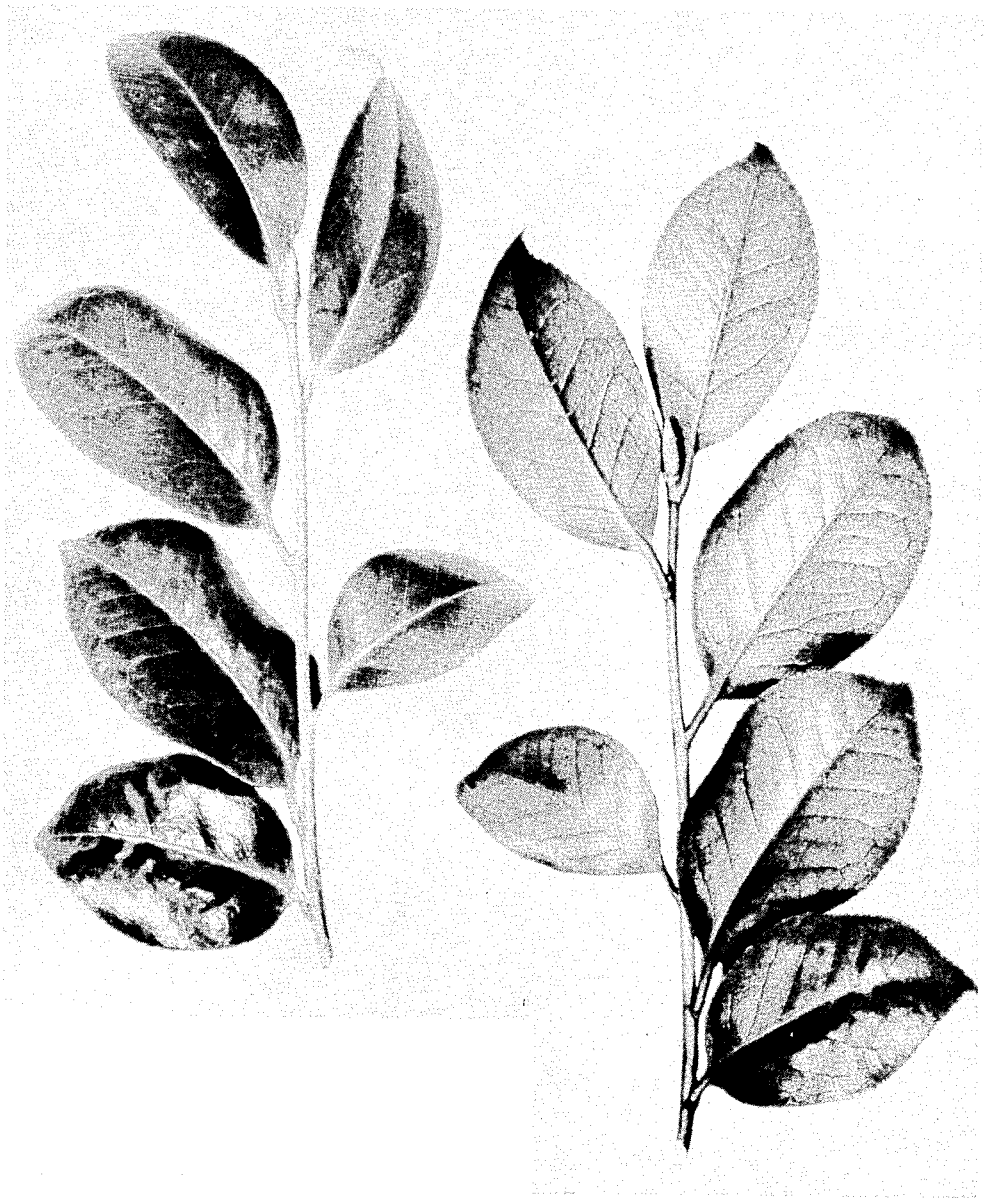
INVENTOR.
E. B. Arnesen
BY Robbat & Cobb
Attorneys.

United States Patent Office

Plant Pat. 1,562
Patented Feb. 12, 1957

1,562

CAMELLIA PLANT

Edward B. Arnesen, San Fernando, Calif.

Application May 21, 1956, Serial No. 586,336

1 Claim. (Cl. 47—60)

The present invention relates to a new and distinct variety of Camellia plant which originated as a sport of the variety known as "Bleichroeder" (unpatented). At the time of my discovery of the new sport, I was cultivating plants of the "Bleichroeder" variety on my property at San Fernando, California. During such cultivation, my attention was attracted to one plane which bore flowers of a color that was unique and entirely different from the normal color of the flowers of "Bleichroeder," which normally are solid white, with pencil stripings of pink, are fully double and have regularly arranged and imbricated petals.

Upon closer examination of the plant which attracted my attention, I found that the parent plant had sported, whereupon, I promptly took steps to preserve the sport and asexually reproduce it to determine whether the new color characteristics of the sport were fixed and transmissible by asexual propagation. Such asexual propagation was performed by me by grafting, at San Fernando, California, and fully confirmed that the new color characteristics of the sport were fixed and established and were transmissible through succeeding propagations.

Continued observations and tests of the new sport conclusively demonstrated that it is generally similar to the parent variety, including similar double, imbricated characteristics of the flowers, but the flowers of the sport are Rhodamine Pink in color, a color unique in the species *Camellia japonica* and usually being found only in the species *C. sasanqua* or *C. reticulata*. This color characteristic is retained despite geographical location, different cultural practices, and widely differing climatical conditions, and is unique, according to qualified experts who have extensively tested and observed my new variety. Because of the striking color difference, which is the principal feature of novelty of the new variety, it is definitely distinguished from all other varieties of which I am aware.

Asexual reproduction of my new variety by grafting at San Fernando, California, shows that the foregoing characteristics and distinctions come true to form and are established and transmitted through succeeding propagations.

The accompanying drawings show typical specimens of the flowers and foliage of my new variety, one of said drawings being depicted in color and showing a fully-opened mature flower, and the other drawing being depicted in black-and-white and showing typical foliage specimens as observed from the upper and lower sides of the foliage.

The following is a detailed description of my new variety, as based upon specimens grown and observed at San Fernando, California, with color terminology in accordance with the Horticultural Chart issued by the British Color Council in collaboration with the Royal Horticultural Society, except where general color terms of ordinary dictionary significance are obvious:

Parentage: Sport of "Bleichroeder."

*Flower*

Blooming habit: Early; December through March.
Bud:

*Size.*—Medium.
*Form.*—Sub-globular.
*Sepals.*—Aspherical; heavily cupped; outer with brown margins; inner with translucent margins.
*Calyx.*—Shape—cupped. Size—about 4.5 cm.

Bloom:
*Size (when fully opened).*—From 3½ inches to 4½ inches.
*Borne.*—Sometimes singly, and sometimes from two to several per stem; on normal stems.
*Form.*—When first petal opens—complete double. When fully opened—rose form.
*Petalage.*—Double; arranged regularly.
*Color.*—Rhodamine Pink, Plate 527/2, with outer petals (guard) from Camellia, Plate 622/1 to Camellia, Plate 622/2.

Petals:
*Texture.*—Firm; satiny.
*Shape.*—Nearly obovate.
*Arrangement.*—Imbricated with channeling, ending in strong haft.
*Lasting quality.*—On plant—from 5 to 7 days. As cut flowers—from 3 to 5 days.

*Genital organs*

Stamens, anthers: Medium-small: many.
*Arrangement.*—Loosely arranged.
*Color.*—White.
Stamens, filaments: Long (up to 2.5 cm. in length); column of crinkled stamens united ⅓ of length. Color—white.
Pollen: Color—golden yellow.
Styles: Malformed; about 1.3 cm. long. Color—white.
Ovaries: All enclosed in calyx.

*Plant*

Form: Shrub.
Growth: Medium vigorous; upright-branching; compact.
Foliage:
*Size.*—Large; blade averages about 8.5 cm. long and about 4.5 cm. wide.
*Quantity.*—Normal.
*Color.*—Mature foliage: upper surface—Spinach Green, Plate 0960; under surface—Fern Green, Plate 0862/1. New foliage: upper surface—Lettuce Green, Plate 861; under surface—Lettuce Green, Plate 861/1.
*Shape.*—From elliptic to broad elliptic.
*Texture.*—Upper surface—glossy; medium heavy; flexible. Under surface—smooth.
*Ribs and veins.*—Prominent.
*Edge.*—Serrated; slightly cupped.
Disease and insect resistance: Comparable to average *japonica* varieties, as determined by comparison with the latter as grown under comparable cultural conditions at San Fernando, California.
Wood:
*New wood.*—Color—from light to golden brown.
*Old wood.*—Color—greyish brown.

I claim:

A new and distinct variety of Camellia plant of the double, imbricated petal type, substantially as herein shown and described, characterized particularly as to novelty by its general similarity to its parent variety "Bleichroeder" (unpatented), combined with a Rhodamine Pink general color tonality of its flowers which differentiates the flowers from the normally solid white color with pencil stripings of pink of the flowers of the parent variety aforesaid.

No references cited.